United States Patent
Aronov

(10) Patent No.: US 8,459,995 B1
(45) Date of Patent: Jun. 11, 2013

(54) PINLESS DENTAL ARTICULATOR AND METHOD OF USING SAME

(76) Inventor: Ilya Aronov, Flushing, NY (US)

( * ) Notice: Subject to any disclaimer, the term of this patent is extended or adjusted under 35 U.S.C. 154(b) by 0 days.

(21) Appl. No.: 13/507,626

(22) Filed: Jul. 16, 2012

(51) Int. Cl.
- *A61C 11/02* (2006.01)
- *A61C 11/08* (2006.01)
- *A61C 13/34* (2006.01)

(52) U.S. Cl.
USPC .......... 433/213; 433/34; 433/54; 433/60

(58) Field of Classification Search
USPC ............ 433/54–67, 34, 72, 74, 75, 213, 214, 433/37, 45, 47, 49; 249/54
See application file for complete search history.

(56) References Cited

U.S. PATENT DOCUMENTS

| | | | |
|---|---|---|---|
| 537,812 A | 4/1895 | Bragg | |
| 3,466,750 A * | 9/1969 | Timberlake et al. | 433/67 |
| 4,203,219 A * | 5/1980 | Wiener | 433/74 |
| 4,439,151 A | 3/1984 | Whelan | |
| 4,538,987 A * | 9/1985 | Weissman | 433/60 |
| 4,898,359 A * | 2/1990 | Gopon | 249/54 |
| 5,506,095 A | 4/1996 | Callne | |
| 5,658,143 A | 8/1997 | Kuperman | |
| 5,996,963 A * | 12/1999 | Michael | 249/54 |
| 6,402,513 B1 * | 6/2002 | Sim | 433/57 |
| 6,910,888 B2 * | 6/2005 | Garland | 433/34 |
| D566,281 S * | 4/2008 | Huffman | D24/182 |
| 2006/0204920 A1 | 9/2006 | Costello | |
| 2007/0231770 A1 * | 10/2007 | Huffman | 433/60 |

FOREIGN PATENT DOCUMENTS

EP 0629385 A1 * 12/1994

OTHER PUBLICATIONS

Garland, James, "New Monotrac V2 Pinless, Cast in Place Articuation", Spectrum dialogue, vol. 5 No. 3, 2006.*
Garland, James, "Going Pinless", Spectrum dialouge, vol. 8, No. 2, Feb. 2009.*
Pearson, "Articulators", Laboratory Catalog, 2011, pp. 65 & 66.
Hydroponics Systems; "CBite Plastic Articulators Dental Lab"; Feb. 15, 2012; www.hydroponicsonline.com/store.

* cited by examiner

*Primary Examiner* — Todd Manahan
*Assistant Examiner* — Michael R Ballinger
(74) *Attorney, Agent, or Firm* — Joseph Scafetta Jr.

(57) ABSTRACT

A pinless dental articulator includes a work tray, a retention pocket, and a monorail formed by a plurality of upwardly tapering cylinders which allow jelly or stone to slide out of the retention pocket when the work tray is turned upside down. The work tray has a ledge which stabilizes a rotatable arm that retains the jelly or stone in the retention pocket. A method of using the articulator includes the steps of installing the locking arm onto the stabilizing ledge of the work tray, rotating the locking arm into a closed position on the stabilizing ledge, pouring jelly into the retention pocket, installing a height-adjusting post in the work tray, tightening a fastener against the post in order to keep the post in an upright position, and placing a small tray with at least one negative tooth impression on top of the jelly.

20 Claims, 9 Drawing Sheets

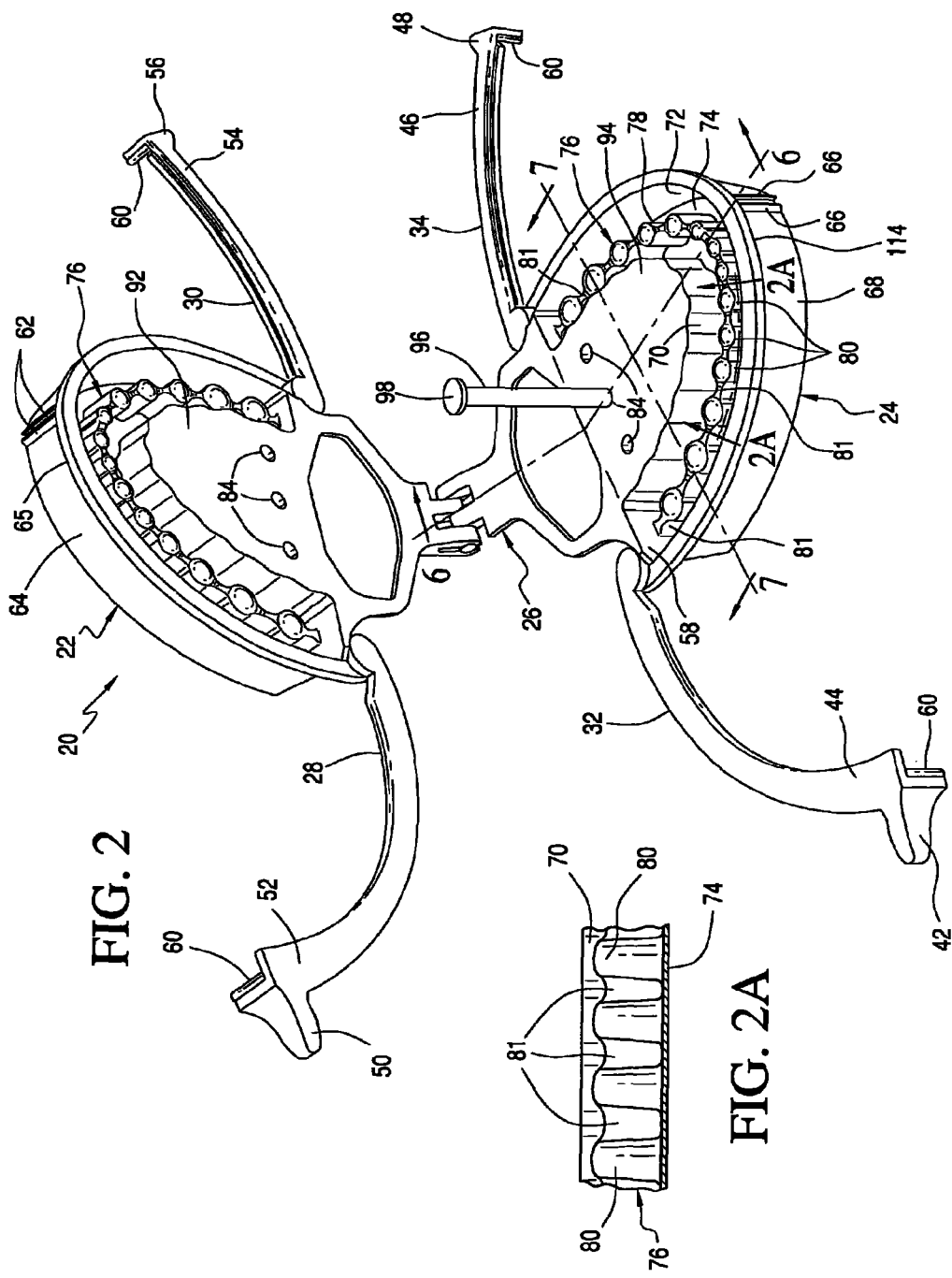

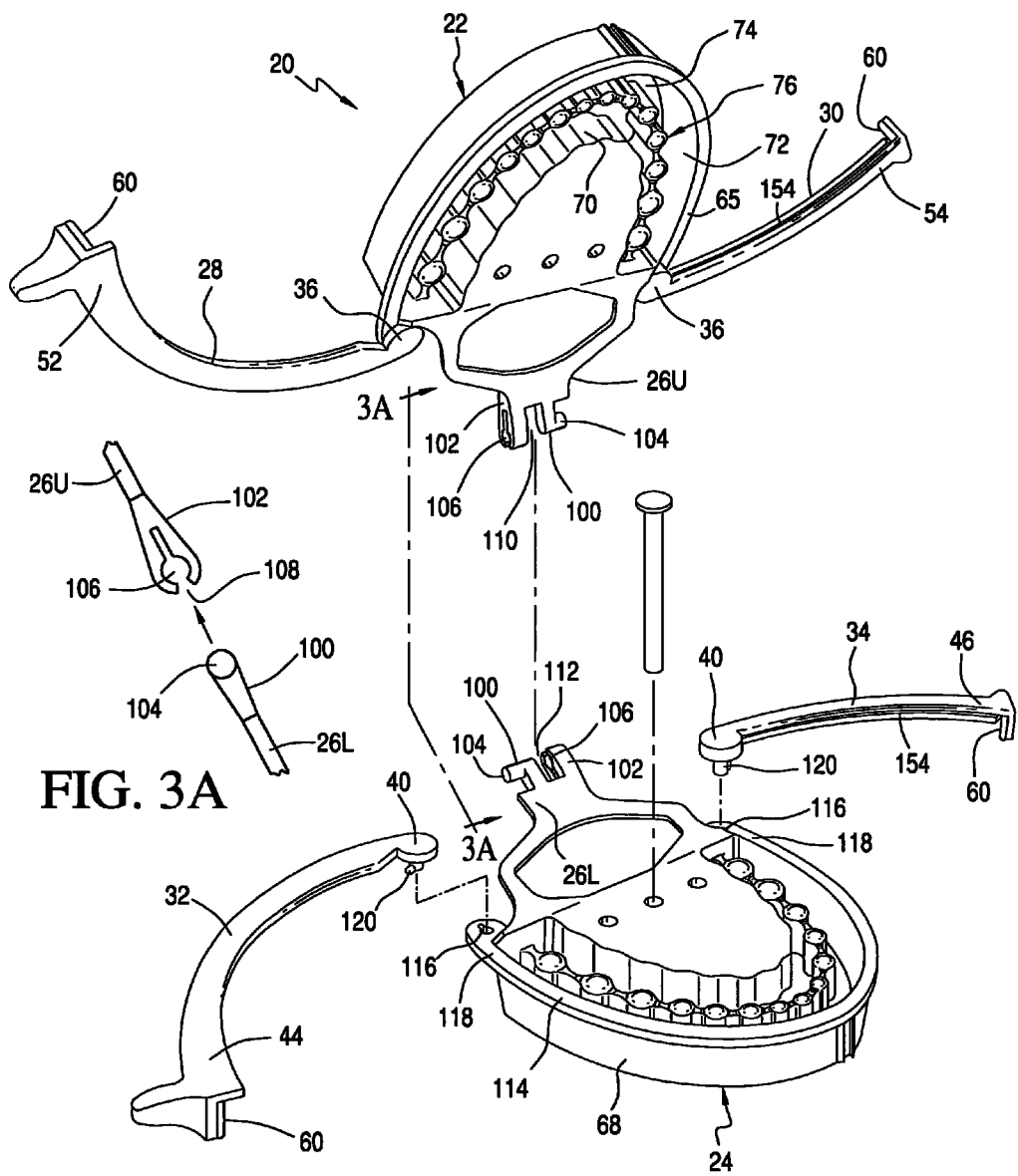

PINLESS DENTAL ARTICULATOR AND METHOD OF USING SAME

CROSS-REFERENCE TO RELATED APPLICATIONS

There are no related applications.

STATEMENT REGARDING FEDERALLY SPONSORED R & D

This application is not the subject of any federally sponsored research or development.

STATEMENT REGARDING JOINT RESEARCH AGREEMENTS

This application is not the subject of any joint research agreement.

BACKGROUND OF THE INVENTION (1) Field of the Invention

The field of this invention encompasses dental articulators and methods for using them.

(2) Description of the Prior Art

Articulators have been utilized in the dental industry since at least the nineteenth century. Basically, they are used by technicians to make artificial dentures.

Early hinged articulators are found in U.S. Pat. No. 537,812 which was issued to Bragg on Apr. 23, 1895. Bragg's invention combined the articulators and vulcanizing flasks.

Towards the end of the twentieth century, a number of relevant improvements were made.

For example, in U.S. Pat. No. 4,439,151, which was issued to Whelan on Mar. 27, 1984, the hinged articulators included a pair of curved trays, each having an upwardly extending portion which extended from a base of the curved tray. See FIGS. 1 and 4, in particular.

U.S. Pat. No. 5,506,095 was issued to Callne on Apr. 9, 1996, for a dental cast tray subassembly hinged to another tray subassembly to form an articulator. Each subassembly included an elongated arcuate protuberance extending from a bottom wall within a canal of the subassembly. This feature is shown best in FIGS. 2-4.

Eventually, manufacturers began to make more complex dental articulators which used multiple pins. However, these pins often fell out and frustrated dental technicians. Two examples are discussed below.

U.S. Pat. No. 5,658,143 was issued to Kuperman on Aug. 19, 1997, for a hinged articulator. Each arch had both dowel and support pins.

U.S. Patent Application No. 2006/0204920 was published in the name of Costello on Sep. 14, 2006, for a hinged articulator. Each tray support had a curved or arching wall. FIG. 1 depicts a hinged articulator in a closed position. Note the use of numerous pins.

Currently available commercial products for dental technicians are depicted in the Pearson 2011 Laboratory Catalog. Articulators are illustrated on pages 65 and 66. Relevant examples are G-Base disposable articulators, Dental Ventures plastic glue-on articulators, Premier disposable articulators, and Mono Trac articulation models.

Hydroponic Systems sells online its C Bite plastic articulators at hydroponicsonline.com/store/CBITE directly to dental labs.

Despite all of these advances, it remains a problem for dental labs to use an articulator which is uncomplicated and easy to manipulate.

BRIEF SUMMARY OF THE INVENTION

An improved articulator hinges together two trays for use in replication of a patient's teeth. A mold of the teeth is made by a conventional impression. Upper and lower trays allow a dental technician to work comfortably and easily without the use of pins to create a model of the patient's teeth when the two separate trays are hinged together.

BRIEF DESCRIPTION OF THE DRAWINGS

FIG. 2 is a perspective view of the first embodiment opened without teeth impressions in place.

FIG. 2A is a detailed side view of part of FIG. 2.

FIG. 3 is an exploded perspective view of the first embodiment opened without teeth impressions in place.

FIG. 3A is a cross-sectional view taken along line 3A-3A in FIG. 3.

DETAILED DESCRIPTION OF PREFERRED EMBODIMENTS

Figure 1:
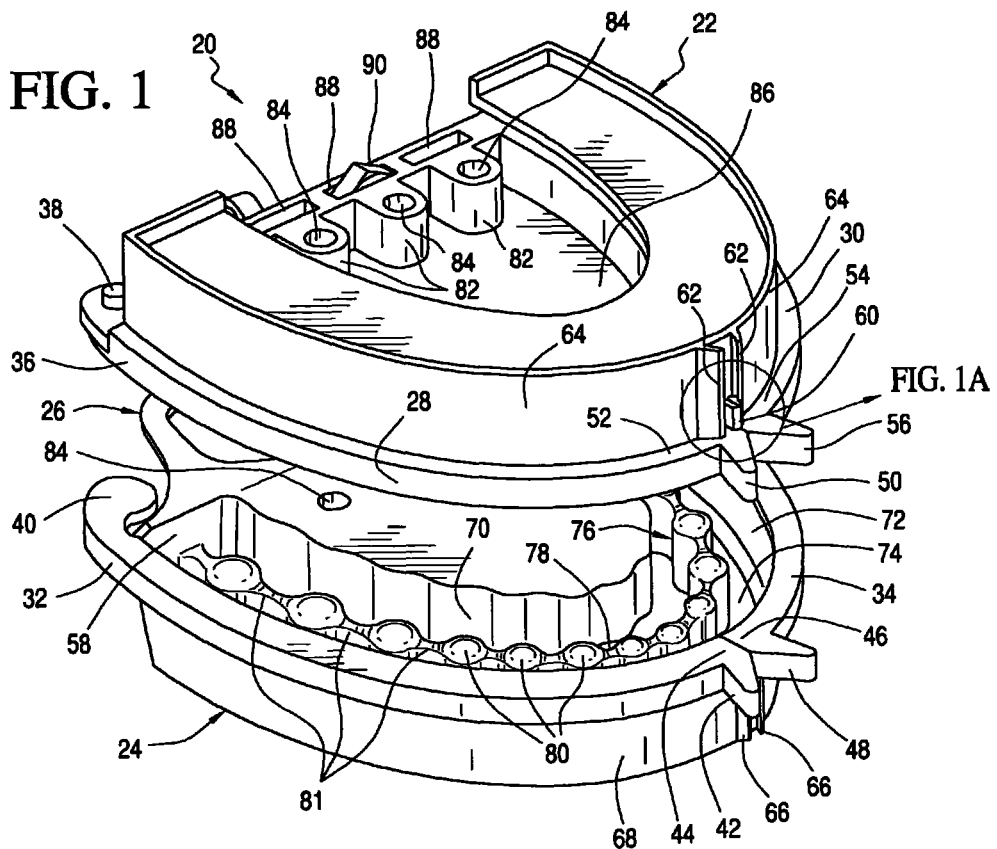
FIG. 1 is a perspective view of a first embodiment of the invention closed without teeth and stone in place.

In FIG. 1, a closed, full-arch articulator 20 has an upper maxillary tray 22 and a lower mandibular tray 24 connected together by a hinge 26 which is only partially shown. The trays 22 and 24 are mirror images of each other. The articulator 20 is made of durable, strong plastic.

The upper tray 22 has a top, left-side, locking arm 28 and a top, right-side, locking arm 30 while the lower tray 24 has a bottom, left-side, locking arm 32 and a bottom, right-side, locking arm 34. The arms 28, 30, 32 and 34 are made of semi-rigid plastic. As an example, the top, left-side arm 28 is secured at its rear end 36 to the tray 22 by a pivoting key pin 38. The bottom, left-side arm 32 is secured to the lower tray 24 at its rear end 40 but a pivoting key pin for the arm 32 is not shown. The bottom, left-side arm 32 has a tab 42 at its front end 44 which contacts a front end 46 adjacent to a tab 48 on the bottom, right-side arm 34. Similarly, the top, left-side arm 28 has a tab 50 at its front end 52 which contacts a front end 54 adjacent to a tab 56 on the top, right-side arm 30. The front end 52 of the top, left-side arm 28 and the front end 54 of the top, right-side arm 30 each has an upwardly extending, flexible pin 60 which snaps over a pair of rigid flanges 62 extending from an outer front wall 64 of the upper tray 22. When the technician pushes the tabs 50 and 56 together with his or her thumbs, the flexible pins 60 snap over the rigid flanges 62 so that the arms 28 and 30 are secured in place along the outer front wall 64 of the upper tray 22. When the technician pushes the tabs 50 and 56 apart using his or her thumbs, the flexible pins 60 roll back over the rigid flanges 62 so that the arms 28 and 30 swing out and turn around their pivot pins 38 at their rear ends 36. The lower tray 24 has rigid flanges 66 on its outer front wall 68. The rigid flanges 66 interact with pins (not shown) on the front ends 44 and 46 of the bottom arms 32 and 34, respectively, to secure the bottom arms 32 and 34 at their rear ends 40. The technician pushes the tabs 42 and 48 together to achieve this result. When the technician pushes the tabs 42 and 48 apart, the bottom arms 32 and 34 are swung outwardly around pivot pins (not shown) at their rear ends 40.

The lower tray 24 has an inner peripheral wall 70, an outer peripheral wall 72 and a floor 74 on which a monorail 76 is centered equidistantly between the peripheral walls 70 and 72. The monorail 76 has a central track 78 along which there are spaced a plurality of upstanding cylinders 80 connected together by a plurality of thin webs 81. The cylinders 80 are upwardly tapered from the floor 74 to their tops. The cylinders are spaced closer together starting from an internal rear wall 58 inside the lower tray 24 and become closer together as the cylinders 80 approach a front of the floor 74 inside the lower tray 24. The upper tray 22 has an identical monorail (not shown). The space in the lower tray 24 between the inner peripheral wall 70, the outer peripheral wall 72 and the floor 74 constitutes a retention pocket into which jelly is poured in order to form a positive dental impression. As the jelly hardens into stone, a groove is formed by the monorail 76 on an underside of the positive dental impression.

Three posts holders 82 have bores 84 vertically through centers of the holders 82 which are arranged on a recessed top side 86 of the upper tray 22. The lower tray 24 has an identical structural arrangement but only one bore 84 is shown. Three rectangular slots 88 are formed next to the post holders 84. A retention bolt 90 is partly shown in the middle slot 88.

Figure 1A:
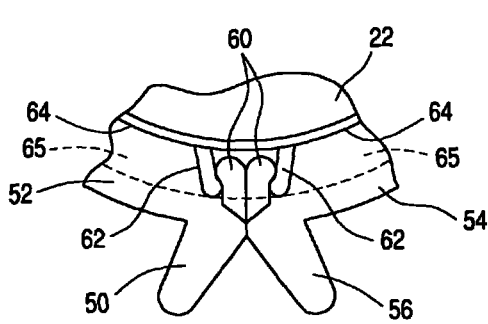
FIG. 1A is a detailed top plan view of a part of FIG. 1 in a closed position.

In FIG. 1A, a detailed top plan view of a part of FIG. 1 in a closed position is shown. The top, left-side arm 28 of FIG. 1 has, in FIG. 1A, its tab 50 at its front end 52 which contacts the front end 54 adjacent to the tab 56 on the top, right-side arm 30 of FIG. 1. In FIG. 1A, the left front end 52 and the right front end 54 each has its own upwardly extending, flexible pin 60 which has snapped over the pair of rigid flanges extending outwardly from the outer front wall 64 and also extending upwardly from a stabilizing ledge 65 shown underneath in phantom lines. The ledge 65 is a stabilizer that extends outwardly from the upper tray 22. When the technician pushes the tabs 50 and 56 together, the flexible pins 60 snap over the rigid flanges 62 so that the front ends 52 and 54 are secured in place along the outer front wall 64 above the stabilizing ledge 65 of the upper tray 22.

Figure 1B:
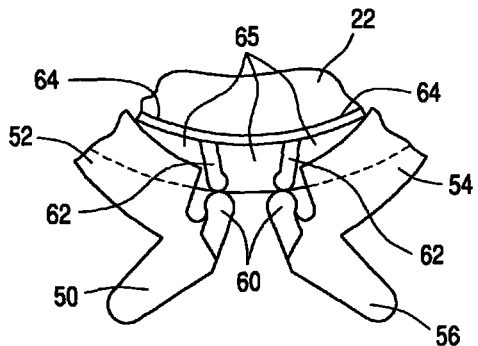
FIG. 1B is a detailed top plan of the same part of FIG. 1 in an opened position.

In FIG. 1B, the technician has pushed the tabs 50 and 56 apart so that the flexible pins 60 are shown in the process of rolling back over the rigid flanges 62. As a result of this opening action, the front ends 52 and 54 have swung out away from the outer front wall 64 so that the underlying, stabilizing ledge 65 of the upper tray 22 is partially visible.

In FIG. 2, a perspective view of the first embodiment, opened without teeth and stone in place, is shown. The opened, full-arch articulator 20 has its upper tray 22 and its lower tray 24 connected together by the hinge 26. The upper tray 22 has its top, left-side, locking arm 28 and its top, right-side, locking arm 30 swung wide open while the lower tray 24 has its bottom, left-side, locking arm 32 and its bottom, right-side, locking arm 34 also swung wide open. The bottom, left-side arm 32 has its tab 42 at its front end 44. The bottom, right-side arm 34 has its tab 48 at its front end 46. Likewise, the top, left-side arm 28 has its tab 50 at its front end 52. The top, right-side arm 34 has its tab 56 at its front end 54. The front end 52 of the top, left-side arm 28 and the front end 54 of the top, right-side arm 30 each has its upwardly extending, flexible pin 60 which has already snapped out over the pair of rigid flanges 62 on the outer front wall 64 above the stabilizing ledge 65 of the upper tray 22 because the technician has swung the arms 28 and 30 out from their closed positions shown in FIGS. 1 and 1A into their opened positions shown in FIGS. 1B and 2. Likewise, the lower tray 24 has its rigid flanges 66 on its outer front wall 68 below a ledge 114 which is a stabilizer. The flexible pins 60 on the front ends 44 and 46 of the bottom arms 32 and 34, respectively, have already rolled over the rigid flanges 66 because the technician has swung the arms 32 and 34 out from their closed positions shown in FIG. 1 into their opened positions shown in FIG. 2.

In FIG. 2, the three bores 84 extend vertically through a flat, bottom side 92 of the upper tray 22. The lower tray 24 has the same three bores 84 extending vertically through a flat, top side 94. A post 96 with a flat, top head 98 is secured into one of the bores 84 made in the flat, top side 94 of the lower tray 24. The height of the post 96 is adjusted so that its head 98 contacts the flat, bottom side 92 of the upper tray 22 when the articulator 20 is closed, as shown in FIG. 1.

In FIG. 2, the hinge 26 is shown connected together for allowing the upper tray 22 and the lower tray 24 to pivot about the hinge 26 from the closed position shown in FIG. 1 into the opened position shown in FIG. 2 and vice versa.

In FIG. 2, the lower tray 24 has the inner peripheral wall 70, the outer peripheral wall 72 and the floor 74 on which the monorail 76 is centered equidistantly between the peripheral walls 70 and 72. The monorail 76 has its central track 78 along which there are spaced the plurality of upwardly tapering cylinders 80 connected together by the plurality of thin webs 81. The cylinders 80 are spaced closer together starting from the internal rear wall 58 inside the lower tray 24 as the cylinders 80 approach towards the front of the floor 74 inside the lower tray 24. The upper tray 22 has an identical monorail 76. The space in the lower tray 24 between the inner peripheral wall 70, the outer peripheral wall 72 and the floor 74 constitutes a retention pocket into which jelly is poured in order to form a positive dental impression. As the jelly hardens into stone, a groove is formed by the monorail 76 on an underside of the positive dental impression.

In FIG. 2A, a detailed side view of part of FIG. 2 is shown. Each of the upstanding cylinders 80 along the monorail 76 has a slight taper as the cylinder 80 rises from the floor 74. The reason for the taper is to allow the stone which has hardened from the jelly to be easily slipped up and out of the retention pocket formed between the floor 74, the inner peripheral wall 70 and the outer peripheral wall 72 (not shown in FIG. 2A but see FIG. 2). The plurality of the thin webs 81, shown in both FIGS. 2 and 2A, also facilitates the release of the stone from the retention pocket. Tops and side surfaces of the cylinders 80 and the webs 81 are undulated so as to allow the jelly or stone to slide out of the retention pocket when the tray 24 is turned upside down. These undulated tops and side surfaces are clearly shown in both FIGS. 2 and 2A. Note that, in the bottom half of FIG. 2, the inner peripheral wall 70 also has an undulating side surface which assists the cylinders 80 and the webs 81 in allowing the jelly or stone to slide out of the retention pocket when the tray 24 is turned upside down.

In FIG. 3, an exploded perspective view of the articulator 20 is shown. The upper tray 22 has its arms 28 and 30 swung wide open. The monorail 76 is centered in the retention pocket formed above the floor 74 between the inner peripheral wall 70 and the outer peripheral wall 72.

The upper tray 22 has a downwardly bent hinge 26U which has an L-shaped male connector 100 and a female connector 102. The male connector 100 has a cylindrical projection 104 while the female connector 102 has a keyhole-shaped opening 106. The lower tray 24 has an upwardly bent hinge 26L which has the same L-shaped male connector 100 with the cylindrical projection 104 and the same female connector 102 with the keyhole-shaped opening 106. The downwardly bent hinge 26U of the upper tray 22 and the upwardly bent hinge 26L of the lower tray 24 are joined together to form the hinge 26 shown in FIG. 2. The joining together is done by forcing the cylindrical projection 104 of the male connector 100 into the keyhole-shaped opening 106 of the female connector 102.

FIG. 3A shows a cross-sectional view through the hinges 26L and 26U of FIG. 3. As is best shown in FIG. 3A, the forcing of the projection 104 into the opening 106 is accomplished because the female connector 102 is made of semi-rigid plastic and has a slit 108 at its open end into which the projection 104 of the male connector 100 can be slipped.

Returning to FIG. 3, when the hinge 26U of the upper tray 22 and the hinge 26L of the lower tray 24 are joined together, the connection between the hinges 26L and 26U is tight. A bight 110 of the upper hinge 26U is plugged with the male connector 100 of the lower hinge 26L. Likewise, a bight 112 of the lower hinge 26L is plugged with the male connector 100 of the upper hinge 26U. See hinge 26 in FIG. 2 for the assembled joint connection.

In FIG. 3, the lower tray 24 also has its arms 32 and 34 swung wide open. Above the outer front wall 68 of the lower tray 24, there is the stabilizing ledge 114 which has a keyhole 116 at each of its rear ends 118. Each of the arms 32 and 34 has a pivoting key pin 120 depending from their rear ends 40. Each key pin 120 fits into each keyhole 116 when the arms 32 and 34 are fully rotated into their opened positions. When the arms 32 and 34 begin to rotate towards their closed positions, the key pins 120 cause the arms 32 and 34 at their rear ends 40 to lock onto the stabilizing ledge 114. This locking onto the stabilizing ledge 114 is accomplished because the arms 32 and 34 each have a longitudinal internal groove 154 into which the stabilizing ledge 114 fits. Although the internal groove 154 of the arm 34 is shown, the internal groove 154 for the arm 32 is hidden in FIG. 3. The arms 28 and 30 of the upper tray 22 have an identical locking arrangement at their rear ends 36 with the pivoting key pin 38 shown in FIG. 1. For the upper tray 22 shown in FIG. 3, the locking onto the stabilizing ledge 65 is accomplished in the same way as for the lower tray 24 because the arms 28 and 30 of the upper tray 22 each have the same longitudinal internal groove 154 into which the stabilizing ledge 65 fits. Although the internal groove 154 of the arm 30 is shown, the internal groove 154 for the arm 28 is hidden in FIG. 3.

When the arms 28 and 30 are fully rotated into their closed positions shown in FIG. 1, the pins 60 at their front ends 52 and 54, respectively, cause the arms 28 and 30 to lock onto the stabilizing ledge 65 shown in FIGS. 1A and 1B. The arms 32 and 34 of the lower tray 24 have an identical locking arrangement at their front ends 44 and 46 with the pins 60 which cause the arms 32 and 34 to lock onto the ledge 114 shown in FIGS. 2 and 3.

Figure 4:
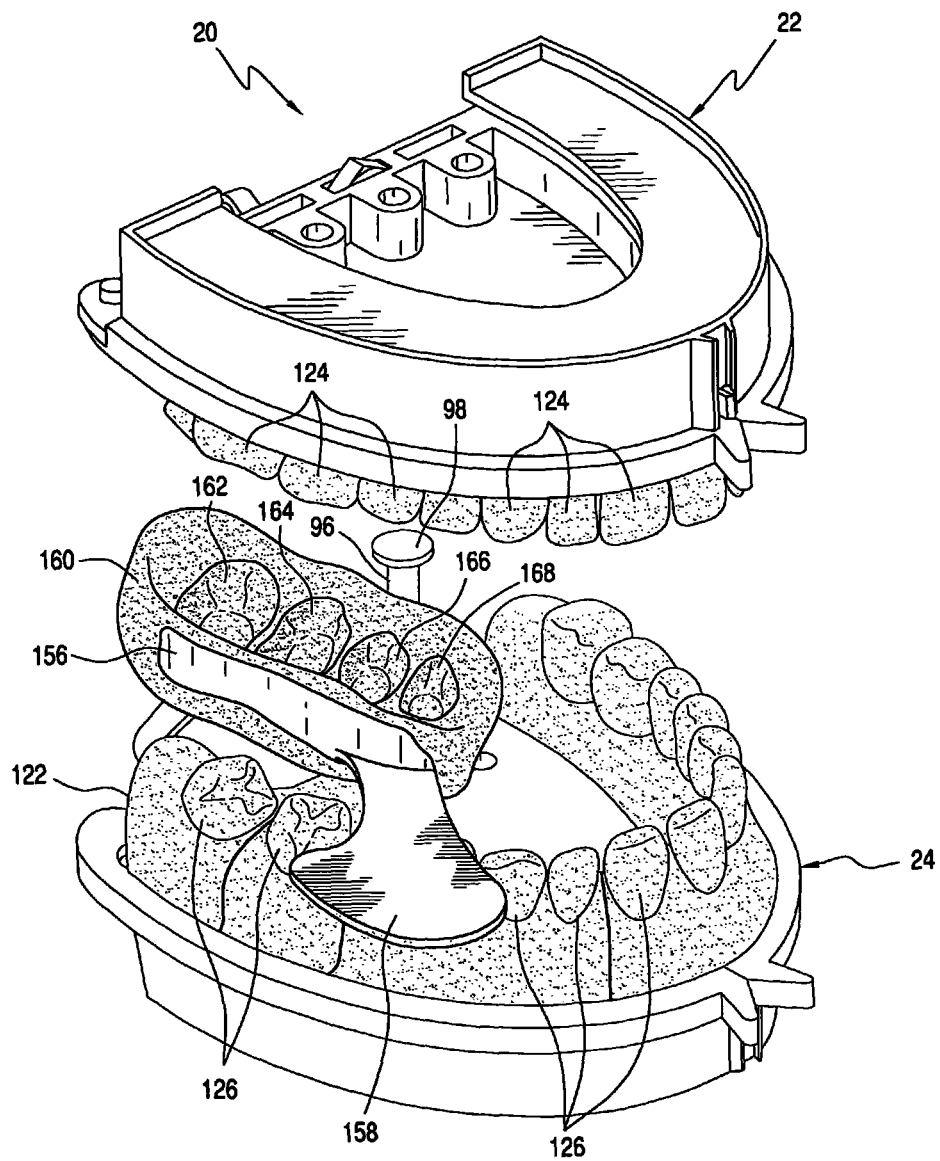
FIG. 4 is an exploded perspective view of the first embodiment with teeth impressions in place.

FIG. 4 shows the articulator 20 with a small tray 156 placed between the upper tray 22 and the lower tray 24 in an exploded perspective view. The small tray 156 has a handle 158. In a dentist's office, when a patient has agreed to have a crown made for a single tooth or a plurality of crowns made for more than one tooth, a dental assistant places some polyurethane plastic 160, shown as stippling, onto either an upper side or a lower side of the small tray 156. In this case, the plastic 160 is placed onto the upper side of the small tray 156. The small tray is then positioned by the dental assistant into the patient's mouth and the patient is asked to bite down onto the small tray 156 so that a negative dental impression is made of the teeth desired to have crowns placed thereon. In this case, negative dental impressions 162, 164, 166 and 168 are formed of the patient's second molar, first molar, second bicuspid and first bicuspid, respectively. After a few minutes, the plastic 160 sufficiently hardens so that the dental assistant can remove the small tray 156 without distorting the negative dental impressions 162 through 168 formed in the plastic 160 on the upper side of the small tray 156. The dental assistant then ships the small tray 156 with the negative dental impressions 162-168 formed in the plastic 160 directly to the dental lab with instructions for the technician to make crowns for the patient's teeth. After the technician loads the retention pocket of the upper tray 22 and, if necessary, the retention pocket of the lower tray 24 with jelly, the technician takes the small tray 156 by the handle 158 and places it between the upper tray 22 and the lower tray 24. The articulator 20 is then closed until the jelly is turned to stone 122, also shown as stippling, in the retention pockets formed in each of the trays 22 and 24. An entire row of positive upper teeth impressions 124 and an entire row of positive lower teeth impressions 126 formed by the stone 122 are shown between the trays 22 and 24, for the sake of completeness. However, usually, only one positive tooth impression is formed or a few positive teeth impressions are formed, as needed, by the stone 122.

Figures 5, 5A:
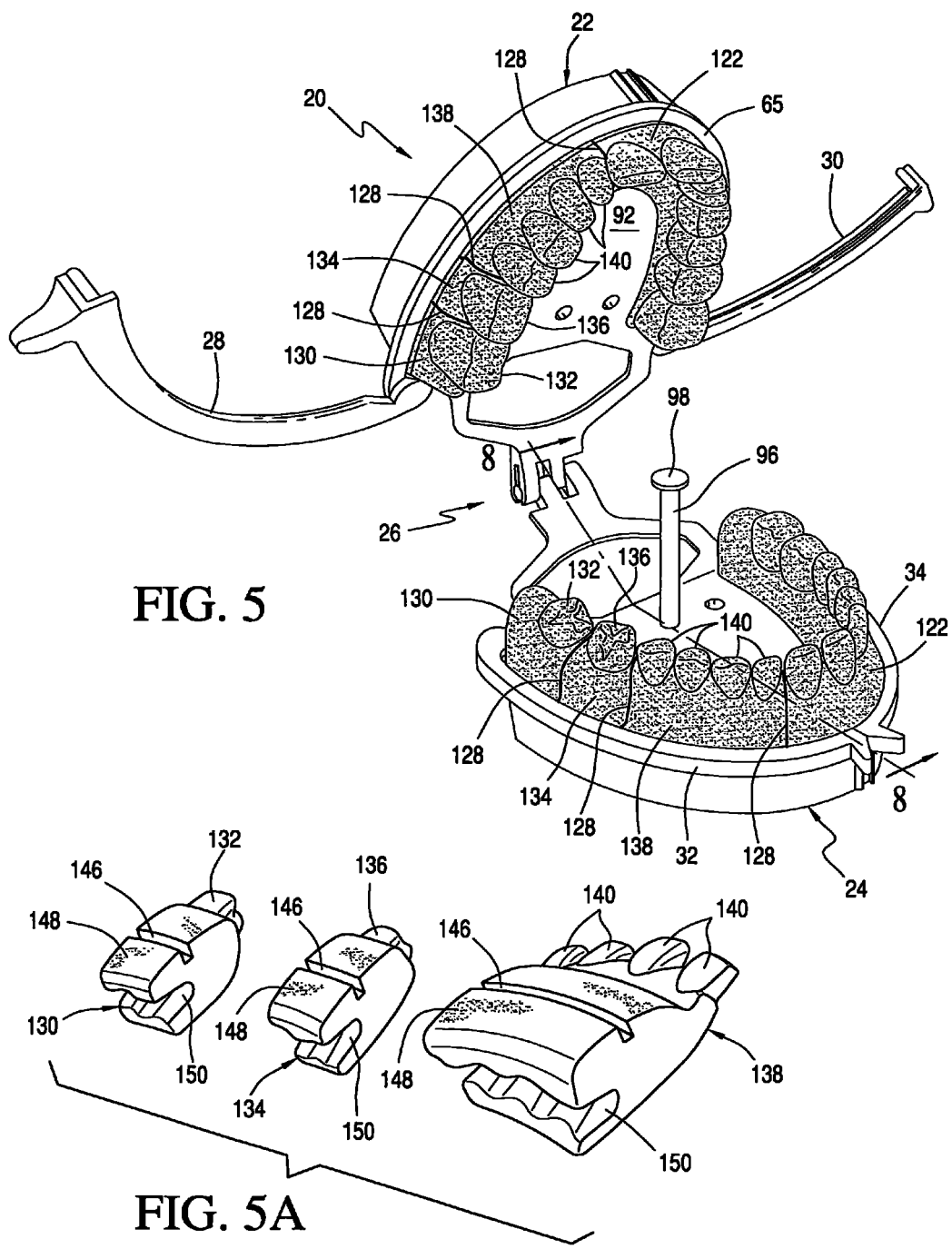
FIG. 5 is a perspective view of the first embodiment opened with teeth impressions in place.
FIG. 5A is an exploded bottom perspective view of the teeth impressions after removal from a retention pocket in a lower tray shown in FIG. 5.

FIG. 5 shows the articulator 20 with the upper tray 22 and the lower tray 24 in their opened positions with the jelly turned to stone 122, again shown as stippling, in the retention pockets formed in each of the trays 22 and 24 which are joined together by the hinge 26. The upper tray 22 has its arms 28 and 30 unlocked and swung wide open while the lower tray 24 has its arms 32 and 34 still locked. A full arch formed by the stone 122 in the upper tray 22 may be removed from the retention pocket by tapping on the flat, bottom side 92 of the upper tray 22 with a small hammer (not shown). After the arch formed by the stone 122 is removed from the retention pocket, the arch may be cut along slice lines 128, selected by the dental technician using a small circular saw (not shown), into sections of one positive tooth impression or a plurality of positive teeth impressions for further work to be done outside of the retention pocket. For example, an end section 130 contains only one second or rear molar tooth impression 132. A penultimate section 134 also contains only a single first or adjacent molar tooth impression 136. However, the next section 138 contains a plurality of positive teeth impressions 140 from back to front for two bicuspids, a cuspid and an incisor, respectively. The further work to be done usually involves taking one section 130, 134 or 138, putting wax on a selected positive tooth impression 132, 136 or 140, respectively, and carving the wax to form a crown. After the wax hardens, the crown has the appearance of tooth enamel. The crown is then sent to the dentist's office with the small tray 156, shown only in FIG. 4. After this further work is done on the teeth 132, 136 or 140 outside of the retention pocket, the positive dental impressions 130, 134 and 138, respectively, are re-inserted into the retention pocket, as shown in the lower tray 24. The arms 32 and 34 of the lower tray 24 are then swung back into their locked positions in order to contain the impressions 130, 134 and 138 in place. Although the same reference numerals are used for the impressions in the upper tray 22 and the lower tray 24, it should be understood that each impression will be shaped differently because no person has teeth which have the exact same shapes in their upper and lower arches.

In FIG. 5A, the sections 130, 134 and 138 with their positive teeth impressions 132, 136 and 140, respectively, have been removed from the lower tray 24 of FIG. 5 and are shown after the stone 122 has been cut along the slice lines 128. In FIG. 5A, each section 130, 134 and 138 has a slit 146 in its outer peripheral surface 148. A groove 150 on an underside of each section 130, 134 and 138 allows each section 130, 134 and 138 to be remounted along the monorail 76, best shown in FIG. 2, at the precise position where it was formed when the jelly was turned to stone 122 in FIG. 5.

Figure 6:
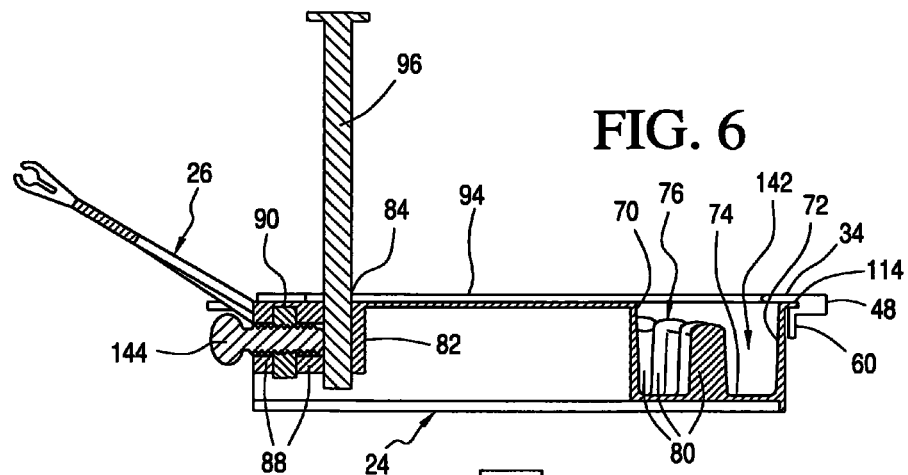
FIG. 6 is a cross-sectional view taken along line 6-6 in FIG. 2.

FIG. 6 is a cross-sectional view taken along line 6-6 through the lower tray 24 and the hinge 26 in FIG. 2. As seen on the right side of FIG. 6, part of the monorail 76 is shown in a retention pocket 142 formed above the floor 74 between the inner peripheral wall 70 and the outer peripheral wall 72. Some of the upstanding, upwardly tapering cylinders 80 forming part of the monorail 76 are also shown. The left-side arm 34 is seen with its front tab 48 and its pin 60 engaged with the stabilizing ledge 114 of the lower tray 24.

As seen on the left side of FIG. 6, the height of the post 96 is adjusted in the bore 84 through the selected post holder 82 so that the post 96 is held vertically in a desired position on the flat, top side 94 of the tray 24. Then, the dental technician manually tightens a fastener, such as a threaded wing bolt 144, perpendicularly through the slot 88 and the retention bolt 90 until the wing bolt 144 presses against a side of the post 96 in order to keep the post 96 upright. The threaded wing bolt 144 may be replaced by a conventional threaded screw with either a Phillips-type head having a cross-shaped slit or an ordinary head having a single slit going across a top of the head. Thus, any type of suitable fastener, like the wing bolt 144, may be used.

Figure 7:
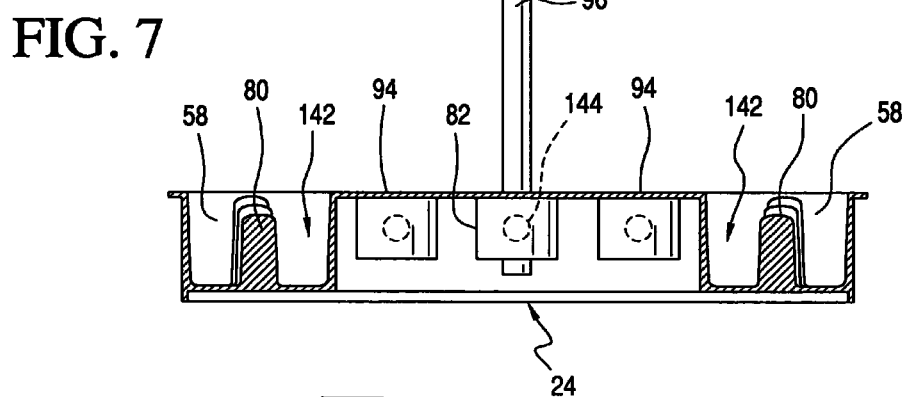
FIG. 7 is a cross-sectional view taken along line 7-7 in FIG. 2.

FIG. 7 is a cross-sectional view of the lower tray 24 taken along line 7-7 in FIG. 2. On the left and right sides of the tray 24, the retention pocket 142 is shown as it appears against the internal, rear wall 58. Some of the upstanding, upwardly tapering cylinders 80 are also seen. The post 96 is secured in the middle post holder 82 on the flat, top side 94 of the tray 24 by the wing bolt 144 of which only its end is seen in phantom lines.

Figure 8:
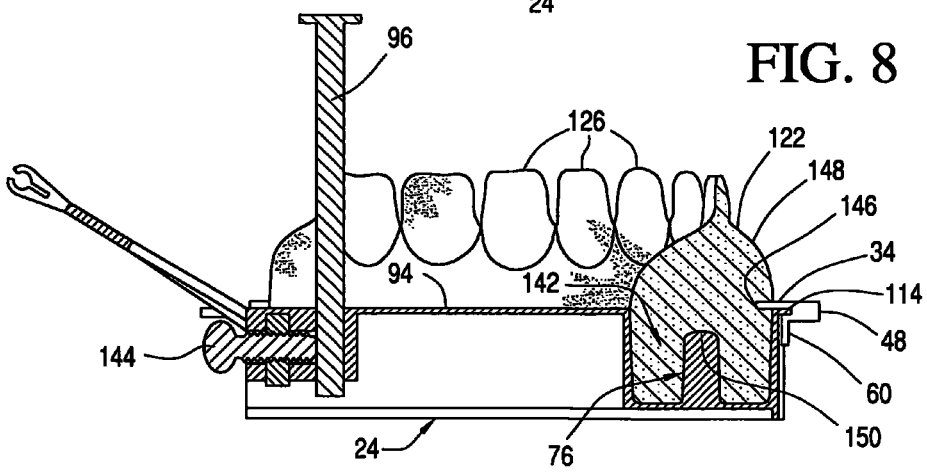
FIG. 8 is a cross-sectional view taken along line 8-8 in FIG. 5.

FIG. 8 is a cross-sectional view of the lower tray 24 taken along line 8-8 of FIG. 5. The left side of FIG. 8 will not be discussed here because it was already discussed above in regard to FIG. 6. In FIG. 8, the retention pocket 142 is filled with jelly which has hardened into the stone 122 which has formed the entire row of the positive lower teeth impressions 126. The stone 122 is held into place because the left-side arm has formed the slit 146 all around the outer peripheral surface 148 of the stone 122. The arm 34 is seen with its front tab 48 and its pin 60 engaged with the stabilizing ledge 114 of the lower tray 24. Also, the stone 122 has the groove 150 formed in its underside by the monorail 76. The stone 122 is removed from the retention groove 142 by swinging the arm 34 out, as shown in FIGS. 2 and 3, and then hitting the flat, top side 94 of the tray 24 with a small hammer to loosen the stone 122 from the monorail 76.

Figure 9:
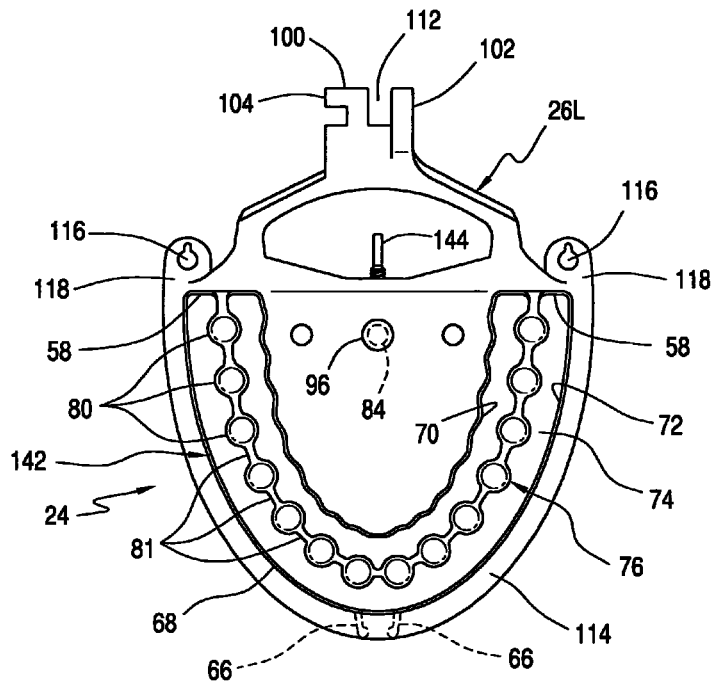
FIG. 9 is a top plan view of the lower tray of the first embodiment.

FIG. 9 is a top plan view of the lower tray 24 without its arms 32 and 34. The tray 24 is shown with its hinge 26L at its rear. The hinge 26L has its bight 112 between the female connector 102 and the male connector 100 with its projection 104. The rigid flanges 66 are seen in phantom lines below the stabilizing ledge 114 which overhangs the outer front wall 68 at the front of the tray 24. At the ends 118 of the stabilizing ledge 114, there are shown the key holes 116 for receiving the pivoting key pins 120 on the underside of the ends 40 of the arms 32 and 34, as best seen in FIG. 3. Returning to FIG. 9, the post 96 is retained in the middle bore 84 and maintained in its upright position by the wing bolt 144, as shown and described in FIG. 6.

Also in FIG. 9, the monorail 76 is centrally positioned in the retention pocket 142 above the floor 74 between the inner peripheral wall 70 and the outer peripheral wall 72. The monorail 76 runs between the rear walls 58 at the left and the right sides of the tray 24. The monorail 76 has its plurality of upstanding, upwardly tapered cylinders 80 connected together by the plurality of thin webs 81. As the monorail 76 approaches from the rear walls 58 towards the front of the tray 24, the webs 81 become shorter in length so that the sections 130, 134 and 138, shown in FIG. 5A, cannot possibly be placed in an incorrect position by the dental technician because the grooves 150, also seen in FIG. 5A, can mount the monorail 76 only at the precise positions where they were formed when the jelly was turned to the stone 122 in the retention groove 142, best seen in FIGS. 6-9.

Figure 10:
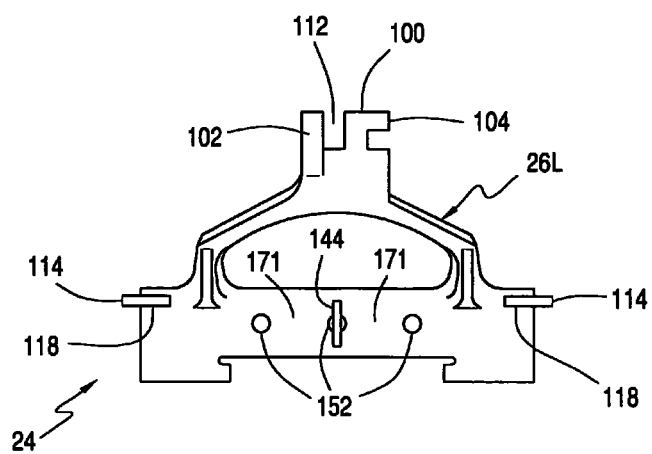
FIG. 10 is a rear elevation view of the lower tray of the first embodiment.

FIG. 10 is a rear elevation view of the lower tray 24 and the hinge 26L. The bight 112 of the hinge 26L is cut between the female connector 102 and the male connector 100 with its projection 104. The stabilizing ledge 114 is seen from its opposite ends 118. Also, the wing bolt 144 is seen from its rear end as it is threaded into a selected one of three bores 152 made in a rear wall 171 in order to maintain upright the post 96, as best seen in FIG. 6.

Figure 11:
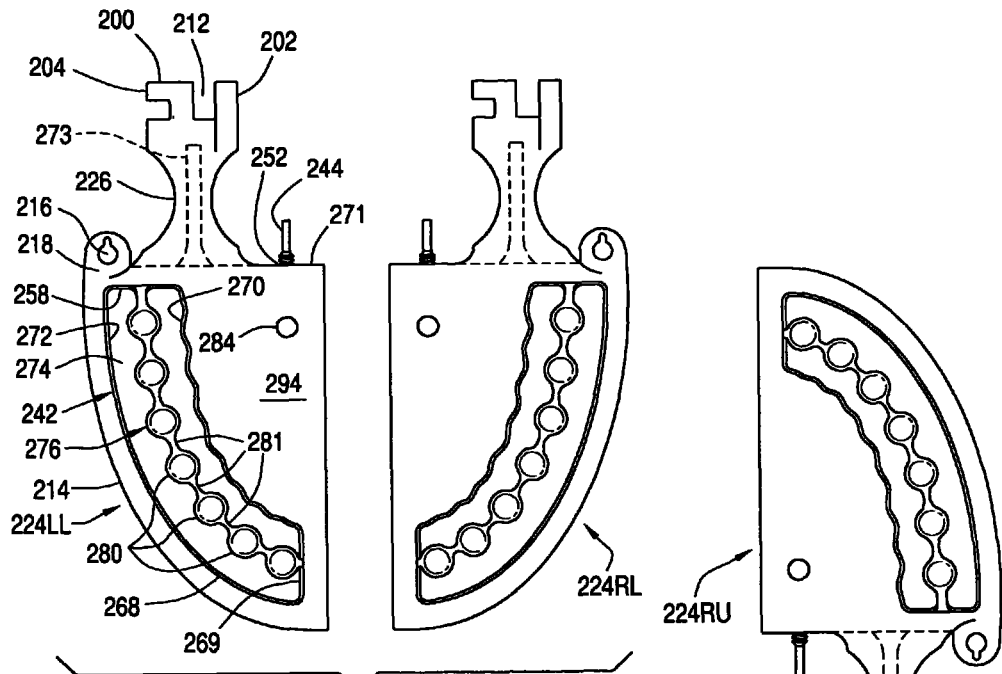
FIG. 11 is a top plan view of a second embodiment which is divided into left and right lower half-arch trays.

FIG. 11 is a top plan view of a second embodiment which is divided into a left lower half-arch tray 224LL and a right lower half-arch tray 224RL. The trays 224LL and 224RL are used to make only one or a few positive teeth impressions. The left half-arch tray 224LL has a retention tray 242 in which there is a monorail 276 formed by a plurality of upstanding, upwardly tapered columns 280 separated by a plurality of thin webs 281. The monorail 276 is formed on a floor 274 between an inner peripheral wall 270 and an outer peripheral wall 272. The monorail 276 is spaced equidistant between the walls 270 and 272. A length of each web 281 becomes shorter, starting from a rear end wall 258 of the retention pocket 276 as the columns 280 approach a front end wall 269 of the retention pocket 276. A single bore 284 is provided through a flat, top side 294 of the tray 224LL. A wing nut 244 is threaded into a bore 252 made in a rear wall 271. A hinge 226 is molded integrally with the rear wall 271 at one end and has, at its opposite end, a male connector 200 and a female connector 202 with a bight 212 between the connectors 200, 202. The male connector 202 has a projection 204 at its far end. The hinge 226, which is also made of plastic, has a metal reinforcing rod 273 molded inside in order to support and strengthen the hinge 226 against breakage during use. The retention pocket 242 has an outer front wall 268 to which there is molded a stabilizing ledge 214. At a rear end 218 of the ledge 214, there is a keyhole 216 into which a pivot pin (not shown) for a locking arm (not shown) is inserted so that the locking arm (not shown) may swing into and out of engagement with the ledge 214. The right lower half-arch tray 224RL is a mirror image of the left lower half-arch tray 224LL and has all of the same elements. Thus, such same elements need not be repeated and described herein.

Figure 12:
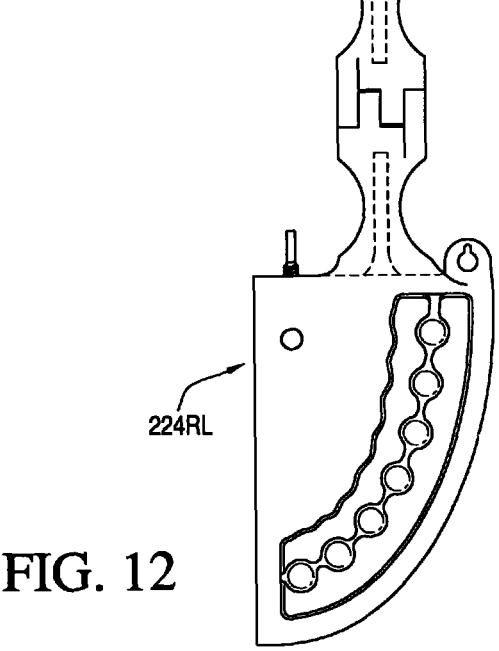
FIG. 12 is a top plan view of the second embodiment which is opened and divided into right upper and lower half-arch trays.

FIG. 12 is a top plan view of the second embodiment which is opened and divided into a right upper half-arch tray 224RU and the right lower half-arch tray 224RL of FIG. 11. It should be noted that the right upper tray 224RU of FIG. 12 is identical to the left lower tray 224LL shown in FIG. 11. In other words, the right upper tray 224RU is simply the left lower tray 224LL flipped around so that the male connector 200 and the female connector 202 of each hinge 226 mate the right upper tray 224RU to the right lower tray 224RL. Also, the right lower tray 224RL of FIGS. 11 and 12 is identical to a left upper tray (not shown). Thus, by using the second embodiment, only two half-arch trays 224LL and 224RL with mating hinges 226 are needed instead of the two full-arch trays 22 and 24 of the first embodiment shown in FIGS. 1-10. Since most dental work involves less than a half arch of teeth, there can be significant cost savings for the dental lab which uses mostly half-arch trays and which has only one or a few full-arch trays on hand for full-arch dental work.

Figure 13:
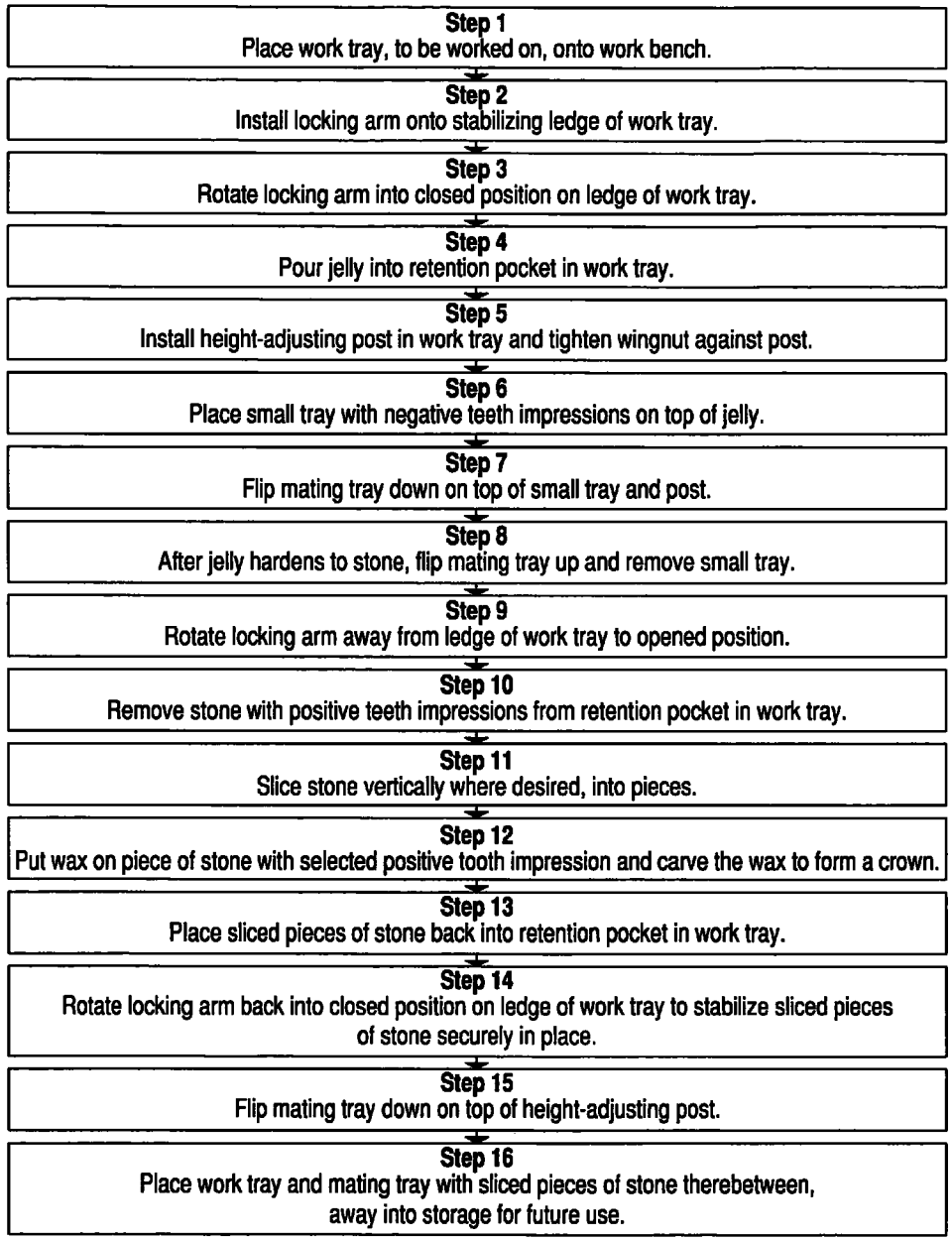
FIG. 13 is a flow chart showing 16 steps of the method for using either the first or second embodiment of the invention.

In FIG. 13, a method for using the invention is illustrated in a flow chart of 16 steps. In step 1, the dental technician places a work tray, to be worked on, onto a work bench. The work tray may be the upper tray 22 or the lower tray 24 of FIG. 1 when the full-arch articulator 20 is being used. When a half-arch articulator is being used, the work tray may be the left lower tray 224LL of FIG. 11, a left upper tray (not shown), the right lower tray 224RL of FIGS. 11 and 12, or the right upper tray 224RU of FIG. 12. To avoid repetition, the rest of the steps of the method will be described solely with reference to the left side of the lower tray 24 of FIG. 1.

In step 2, the technician takes the free locking arm 32 of FIG. 3 and aligns the pivot pin 120 at the end 40 into the key hole 116 at the end 118 of the stabilizing ledge 114 of the tray 24. When the pivot pin 120 goes through the key hole 116, the position of the arm 32 will be as shown in FIG. 2.

In step 3, the technician rotates the locking arm 32 into the closed position, as seen in FIGS. 1, 4 and 5, on the ledge 114 of the tray 24. The ledge 114 is not seen in FIGS. 1, 4 and 5, but it is seen in the opened positions of FIGS. 2, 3 and 9.

In step 4, the technician pours jelly 122, as seen in FIGS. 4, 5 and 8, into the retention pocket 142, best seen in FIGS. 6-9, of the tray 24.

In step 5, the technician installs the height-adjusting post 96, as seen in FIG. 2, into the selected bore 84. As best seen in FIGS. 6 and 8, the technician tightens a fastener, which in this case is the wing bolt 144 against a vertical side of the post 96.

In step 6, the technician takes the small tray 156 by the handle 158, as shown in FIG. 4, and places the small tray 156 with the negative teeth impressions 162-168 on top of the jelly 122 in the lower tray 24. The negative teeth impressions 162-168 on an upper side of the small tray 156 will form positive teeth impressions 124 in the jelly on the upper tray 22. However, if the negative teeth impressions 162-168 are formed on a lower side of the small tray 156, then the positive teeth impressions 126 will be formed in the jelly 122 in the lower tray 24.

In step 7, the technician flips down the upper mating tray 22 of FIGS. 4 and 5 on top of the small tray 156 and the post 96, installed in the lower tray 24, as seen in FIG. 4. The cap 98 on the post 96 stops the upper tray 22 from coming down too far so that damage to the positive teeth impressions 124 and 126 is prevented.

In step 8, after the jelly 122 hardens to stone, the technician flips the mating tray 22 up, as seen in FIG. 5, and removes the small tray 156 seen only in FIG. 4.

In step 9, the technician rotates the locking arm 32 away from the stabilizing ledge 114 from the lower tray 22 in the same manner as the locking arm 28 is shown in FIG. 5 to be rotated away from the stabilizing ledge 65 of the upper tray 22 so that the trays 22 and 24 are in their opened positions.

In step 10, the technician removes the stone with the positive teeth impressions 126, as seen in FIG. 4, from the retention pocket 142, best seen in FIGS. 6-9 in the lower tray 24.

In step 11, the technician slices the stone vertically where desired, for example, along slice lines 128 seen in FIG. 5, into the pieces 130, 134 and 138 shown in FIG. 5A.

In step 12, the technician puts wax on the piece 130, 134 or 138 with the selected positive tooth impression 132, 136 or 140 respectively, and carves the wax to form a crown. After the wax hardens, it has the appearance of tooth enamel and is ready to be shipped to the orthodontist who sent the small tray 156 with the negative teeth impressions 160-168 of FIG. 4.

In step 13, the technician places the sliced pieces 130, 134 and 138 of the stone 148 in FIG. 5A back into the retention pocket 142, best seen in FIGS. 6-9, in the tray 24.

In step 14, the technician rotates the locking arm 32 back into the closed position on the ledge 114 of the tray 24 in the same manner as the locking arm 34 seen in FIG. 8. An edge of the arm 34 protrudes into the groove 146 formed in the stone 148 in order to stabilize the sliced pieces of stone 148 securely in place.

In step 15, the technician flips the mating tray 22, as seen in FIG. 5, down on top of the height-adjusting post 96. The cap 98 on top of the post 96 prevents the mating tray 22 from coming down too far and damaging the positive teeth impressions 132, 136 and 140 formed on the sliced pieces 130, 134 and 138, respectively, retained in the tray 24.

In step 16, the technician places the lower work tray 24 and the upper mating tray 22, with the sliced pieces 130, 134 and 138 therebetween, in the closed position, away into storage for future use.

Thus, a pinless dental articulator and method for using the same has been disclosed. While the invention has been described with two preferred embodiments, many modifications will become readily apparent to those skilled in dental technology after reading the foregoing disclosure.

From the foregoing detailed description of the preferred embodiments, it should be apparent to those skilled in the art of making dental impressions that other constructions and modifications may be made and will still be considered within the scope of the invention.

Therefore, it should be understood that I do not intend to be limited to the two embodiments specifically described above, but it is my intention to be bound only by the scope of the appended claims.

What I claim as my invention is as follows:
1. A dental articulator comprising:
a work tray having a back wall, an inner peripheral wall, and an outer peripheral wall;
a retention pocket configured to retain jelly or stone within the work tray; and
a monorail arranged within the retention pocket between the inner peripheral wall and the outer peripheral wall of the work tray, said monorail including a plurality of upwardly tapering cylinders and a plurality of webs interconnecting the plurality of upwardly tapering cylinders;

wherein tops and side surfaces of the cylinders and the webs are undulated so as to allow the jelly or stone to slide out of the retention pocket when the work tray is turned upside down.

2. The articulator according to claim 1, wherein:
said work tray has an outer wall and a ledge overhanging the outer wall, said ledge having a rear end.

3. The articulator according to claim 2, further comprising:
an arm rotatable about the rear end of the ledge and configured to lock onto the ledge in order to retain jelly or stone in the retention pocket, said arm having a front end.

4. The articulator according to claim 3, wherein:
said outer wall has at least one vertically oriented flange extending therefrom; and
said front end of the arm has a pin which engages with the flange.

5. The articulator according to claim 3, wherein:
said front end of the arm has a tab configured to be gripped when the arm is to be locked onto or unlocked from the ledge.

6. The articulator according to claim 3, wherein:
said arm has a longitudinal groove into which the ledge extends in order to stabilize the arm onto the ledge.

7. The articulator according to claim 1, wherein:
said monorail is spaced equidistantly between the inner peripheral wall and the outer peripheral wall of the work tray, wherein said inner peripheral wall has an undulating side surface which assists the cylinders and webs in allowing the jelly or stone to slide out of the retention pocket when the work tray is turned upside down.

8. The articulator according to claim 1, wherein:
said plurality of upwardly tapering cylinders is spaced closer together the farther the cylinders are positioned from the back wall of the work tray.

9. The articulator according to claim 1 further comprising:
a mating tray; and
a hinge interconnecting the mating tray with the work tray.

10. The articulator according to claim 9, wherein:
said hinge has a male connector and a female connector.

11. The articulator according to claim 10, wherein:
said male connector has a projection and said female connector has a keyhole-shaped opening with a slit configured to receive the projection of the male connector.

12. The articulator according to claim 9, further comprising:
a post arranged in the work tray and configured to be adjusted to a height between the work tray and the mating tray.

13. The articulator according to claim 12, further comprising:
a fastener configured to be tightened against the post in order to keep the post in an upright position.

14. A method of using a dental articulator comprising:
installing a locking arm onto a stabilizing ledge of a work tray having a monorail arranged therein, said monorail including a plurality of upwardly tapering cylinders and a plurality of webs interconnecting the plurality of upwardly tapering cylinders;
rotating the locking arm into a closed position on the stabilizing ledge of the work tray;
pouring jelly into a retention pocket in the work tray;
installing a height-adjusting post in the work tray;
tightening a fastener against the post in order to keep the post in an upright position; and
placing a small tray with at least one negative tooth impression on top of the jelly;
wherein tops and side surfaces of the cylinders and the webs are undulated so as to allow the jelly or stone to slide out of the retention pocket when the work tray is turned upside down.

15. The method according to claim 14, further comprising:
flipping a mating tray down on top of the small tray and the post;
flipping the mating tray up and removing the small tray after the jelly hardens to stone; and
rotating the locking arm away from the stabilizing ledge of the work tray to an opened position.

16. The method according to claim 15, further comprising:
removing stone with at least one positive tooth impression from the retention pocket in the work tray;
slicing the stone vertically, where desired, into pieces;
putting wax on one of the pieces of stone with at least one selected positive tooth impression; and
carving the wax to form a crown.

17. The method according to claim 16, further comprising:
placing sliced pieces of stone back into the retention pocket in the work tray; and
rotating the locking arm back into the closed position on the ledge of the work tray in order to stabilize the sliced pieces of stone securely in place.

18. The method according to claim 17, further comprising:
flipping the mating tray down on top of the height-adjusting post.

19. The method according to claim 18, further comprising:
placing the work tray and the mating tray, with the sliced pieces of stone therebetween, away into storage for future use.

20. The method according to claim 14, wherein:
said monorail is spaced equidistantly between an inner peripheral wall and an outer peripheral wall of the work tray, wherein said inner peripheral wall has an undulating side surface which assists the cylinders and webs in allowing the jelly or stone to slide out of the retention pocket when the work tray is turned upside down.

\* \* \* \* \*